US00PP14249P29

(12) United States Plant Patent
Bradford

(10) Patent No.: US PP14,249 P2
(45) Date of Patent: Oct. 21, 2003

(54) NECTARINE TREE NAMED 'CANDY PEARL'

(50) Latin Name: *Prunus persica*
Varietal Denomination: Candy Pearl

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/299,085

(22) Filed: Nov. 19, 2002

(51) Int. Cl.[7] ..... A01H 5/00
(52) U.S. Cl. ..... Plt./188
(58) Field of Search ..... Plt./188

(56) References Cited

U.S. PATENT DOCUMENTS

PP7,193 P 3/1990 Bradford
PP9,360 P 11/1995 Bradford
PP10,871 P 4/1999 Bradford

*Primary Examiner*—Bruce R. Campell
*Assistant Examiner*—W C Haas

(57) ABSTRACT

The present invention relates to a nectarine tree, *Prunus persica,* and more particularly to a new and distinct variety broadly characterized by a medium size, vigorous, hardy, self-fertile, productive and regular bearing tree. The fruit matures under the ecological conditions described approximately the first week in July, with first picking on Jul. 2, 2002. The fruit is uniformly large in size, excellent in flavor, globose in shape, clingstone in type, very firm in texture, white in flesh color, and red in skin color. The variety was developed as a first generation cross using 'Red Glen' (U.S. Plant Pat. No. 7,193) yellow flesh nectarine as the selected seed parent and 'June Pearl' (U.S. Plant Pat. No. 9,360) white flesh nectarine as the selected pollen parent.

1 Drawing Sheet

Botanical classification: *Prunus persica.*

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'CANDY PEARL'. The present variety was hybridized by me in 1994, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'Red Glen' (U.S. Plant Pat. No. 7,193) yellow flesh nectarine as the selected seed parent and 'June Pearl' (U.S. Plant Pat. No. 9,360) white flesh nectarine as the selected pollen parent. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is similar to its selected seed parent, 'Red Glen' (U.S. Plant Pat. No. 7,193) nectarine, by producing nectarines that are globose in shape, very firm in texture, clingstone in type, and full red in skin color, but is very distinguished therefrom and an improvement thereon by producing fruit that is white instead of yellow in flesh color, that is subacid instead of acid in flavor, and that matures about one month earlier.

The present variety is similar to its selected pollen parent, 'June Pearl' (U.S. Plant Pat. No. 9,360) nectarine, by producing nectarines that are white in flesh color, full red in skin color, and subacid in flavor, but is quite distinguished therefrom and an improvement thereon by producing fruit that is much larger in size and that matures about eighteen days later.

The present variety is most similar to 'Kay Pearl' (U.S. Plant Pat. No. 10,871) nectarine by producing white flesh nectarines that are firm in texture, full red in skin color, and sweet subacid in flavor, but is distinguished therefrom and an improvement thereon by having reniform instead of globose leaf glands and by producing nectarines that are clingstone instead of freestone, that have less skin freckling, that are somewhat larger in size, and that mature about six days later.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 7, 2002, on the original tree during its eighth growing season. All major color code designations are by reference to the Inter-Society Color Council, National Bureau of Standards. Common color names are also used occasionally.

Tree

Size: Medium, reaching a height of 9' [2.74 m.] and a spread of 10' [3.05 m.] after eight growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Vase formed.
Hardiness: Hardy with respect to central California winters.
Heat tolerance: Observed to perform adequately in typical central California climatic conditions, which typically include extended periods of heat.
*Drought tolerance.*—Variety is developed for commercial orchards and requires regular irrigation.
Production: Productive, thinning necessary.
Fertility: Self-fertile.
Bearing: Regular bearer with no alternate bearing yet observed.
Trunk:
*Size.*—Medium, with a maximum diameter of 4" [101 mm.] after the eighth growing season.
*Texture.*—Somewhat shaggy.
*Bark color.*—Dark grayish reddish brown [47. d.gy.rBr].
*Lenticels.*—Approximate Number Per Square Inch: 14. Color: Moderate orange yellow [71. m.OY]. Typical Size: ⅛" to ⅜" [3.2–9.5 mm.].
Branches:
*Size.*—Diameter of limb is 1¼" [32 mm.] measured 12" above the secondary fork, typical of *Prunus persica,* and dependent upon cultural practices and climatic conditions.
*Texture.*—Smooth on 1st year wood, increasing roughness with age.
*Color.*—1st Year Wood Topside: Grayish red [19. gy.R]. 1st Year Wood Underside: Brilliant yellow green [116. brill.YG]. Older Wood: Deep yellowish brown [75. deep yBr].
*Lenticels.*—Approximate Number Per Square Inch: 75. Color: Light orange yellow [70. l.OY]. Typical size: 1/32" to ⅛" [0.8–3.2 mm.].
Leaves:
*Size.*—Medium. Average Length: 5¾" [146 mm.]. Average width: 1½" [38 mm.].
*Arrangement.*—Alternate.
*Thickness.*—Medium.
*Form.*—Elliptical.
*Apex.*—Acuminate.
*Base.*—Acute, with an average base angle of 70 degrees.
*Surface.*—*Smooth.*
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: 7/16" [11.1 mm.]. Average Thickness: 1/16" [1.6 mm.]. Color: Moderate yellow green [120. m.YG].
*Stipules.*—Number: 2 per leaf, up to 6 per growing tip. Average Length: ⅜" [9.5 mm.]. Color: Light yellow green [119. l.YG] with Grayish red [19. gy.R] edges when young and growing, Dark brown [59. d.Br] when old and dry.
*Glands.*—Number: 2 to 4. Position: Mostly alternate, positioned on both the petiole and base of blade. Size: Small. Form: Reniform. Color: Moderate yellow green [120. m.YG] on younger leaves acquiring Moderate reddish brown [43. m.rBr] centers with age.
*Leaf buds.*—Conic.
Flower buds:
*Hardiness.*—Hardy, with respect to central California winters.
*Diameter.*—Typically 5/16" [7.9 mm.] 1 week before bloom.
*Length.*—Typically ½" [12.7 mm.] 1 week before bloom.
*Form.*—Not appressed.
*Surface.*—Pubescent.
*Color.*—Strong purplish red [255. s.pR].
Flowers: Perfect, complete, perigynous, usually a single pistil, typically thirty or more stamens, five sepals and petal locations alternately positioned.
*Type.*—Showy, large.
*Average flower diameter.*—1¾" [44.5 mm.].
*Number of petals.*—Almost always five.
*Petal shape.*—Circular.
*Petal margin.*—Somewhat wavy.
*Average petal diameter.*—¾" [19.1 mm.].
*Average petal length.*—13/16" [20.6 mm.].
*Petal apex.*—Rounded with a small notch located at the top center of the margin on many.
*Petal base.*—Rounded.
*Petal color.*—Light purplish pink [249. l.pPk].
*Anther color.*—Dark red [16. d.R] over a Brilliant orange yellow [67. brill.OY] center.
*Stigma color.*—Light greenish yellow [101. l.gY].
*Sepal color.*—Dark purplish red [259. d.pR].
*Sepal length.*—¼" [6 mm.].
*Sepal width.*—3/16" [5 mm.].
*Average pistil length.*—⅝" [15.9 mm.].
*Average stamen length.*—⅝" [15.9 mm.].
*Fragrance.*—Moderate when nectar is present.
*Blooming period.*—Medium compared with other varieties.
*Onset of bloom.*—One percent on Mar. 3, 2002.
*Date of full bloom.*—Mar. 10, 2002.
*Duration of bloom.*—One to two weeks, dependent on ambient temperature.
*Number per cluster.*—1 to 3 with single flowers most common.

FRUIT

Maturity when described: Firm ripe, Jul. 7, 2002.
Date of first picking: Jul. 2, 2002.
Date of last picking: Jul. 14, 2002.
Size: Uniform, medium.
*Average diameter axially.*—2⅞" [73.0 mm.].
*Average diameter across suture plane.*—2¾" [69.9 mm.].
*Typical weight.*—7.1 ounces [200 grams].
Form: Globose with about fifty percent slightly asymmetrical.
*Longitudinal section form.*—Circular to somewhat oblong.
*Transverse section through diameter.*—Circular.
Suture: A shallow groove near the base becoming deeper toward the apex and ending with a marked depression just beyond the pistil point.
Ventral surface: Rounded, lipped toward the apex.
Lips: Slightly unequal.

Cavity: Flaring, elongated in the suture plane, suture showing on both sides, Yellowish white [92. yWhite] stem markings typical.

*Depth.*—5/8" [15.9 mm.].

*Breadth.*—1" [25.4 mm.].

Base: Truncate and somewhat cuneate when viewed along the suture.

Apex: Rounded and slightly cuneate when viewed along the suture.

Pistil point: Oblique, short, depressed within the suture.

Stem: Medium.

*Average length.*—3/8" [9.5 mm.].

*Average width.*—3/16" [4.8 mm.].

Skin:

*Thickness.*—Medium.

*Surface.*—Smooth.

*Tenacity.*—Tenacious to flesh.

*Astringency.*—Nonastringent.

*Tendency to crack.*—None observed.

*Color.*—Very dark red [17. v.d.R] over a Strong red [12. s.R] background with Pale orange yellow [73. p.OY] freckling on the sides and toward the apex.

Flesh:

*Color.*—White [263. White] with a slight amount of Moderate red [15. m.R] streaking very close to the stone and very slight flecking throughout.

*Surface of pit cavity.*—Moderate red [15. m.R] fibers breaking when twisted from the stone.

*Amygdalin.*—Scarce.

*Juice.*—Abundant, rich.

*Texture.*—Very firm, crisp.

*Fibers.*—Abundant, fine.

*Ripens.*—Slightly earlier toward the apex.

*Flavor.*—Subacid and sweet, averaging 16 brix.

*Aroma.*—Slight.

*Eating quality.*—Excellent.

STONE

Type: Clingstone.

Form: Oval.

Hilum: Narrow, oblong.

Base: Straight.

Apex: Acute, with an average tip angle of 80 degrees.

Sides: Equal.

Surface: Irregularly furrowed near the apex and pitted toward the base.

Ridges: Jagged toward the base.

Color: Moderate reddish brown [43. m.rBr].

Average pit wall thickness: 1/4" [6.4 mm.].

Average width: 1" [25.4 mm.].

Average length: 1 1/2" [38.1 mm.].

Average breadth: 13/16" [20.6 mm.].

Tendency to split: Slight.

Kernel:

*Form.*—Oval.

*Pellicle color.*—Moderate yellowish brown [77. m.yBr].

*Skin color.*—Pale yellow [89. p.Y] when freshly removed.

*Vein color.*—Grayish yellowish brown [80. gy.yBr].

*Taste.*—Sweet.

*Viable.*—Yes.

*Average width.*—1/2" [12.7 mm.].

*Average length.*—13/16" [20.6 mm.].

*Amygdalin.*—Scant.

USE

Market: Fresh market and long distance shipping.

Keeping quality: Good. Fruit quality observed to remain in good condition in after 21 days in standard cold room at 36° Fahrenheit [2° Celsius].

Shipping quality: Good.

Resistance to insects: No unusual susceptibilities noted.

Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Kay Pearl' (U.S. Plant Pat. No. 10,871) nectarine by producing white flesh nectarines that are firm in texture, full red in skin color, and sweet subacid in flavor, but is distinguished therefrom and an improvement thereon by having reniform instead of globose leaf glands and by producing nectarines that are clingstone instead of freestone, that have less skin freckling, that are somewhat larger in size, and that mature about six days later.

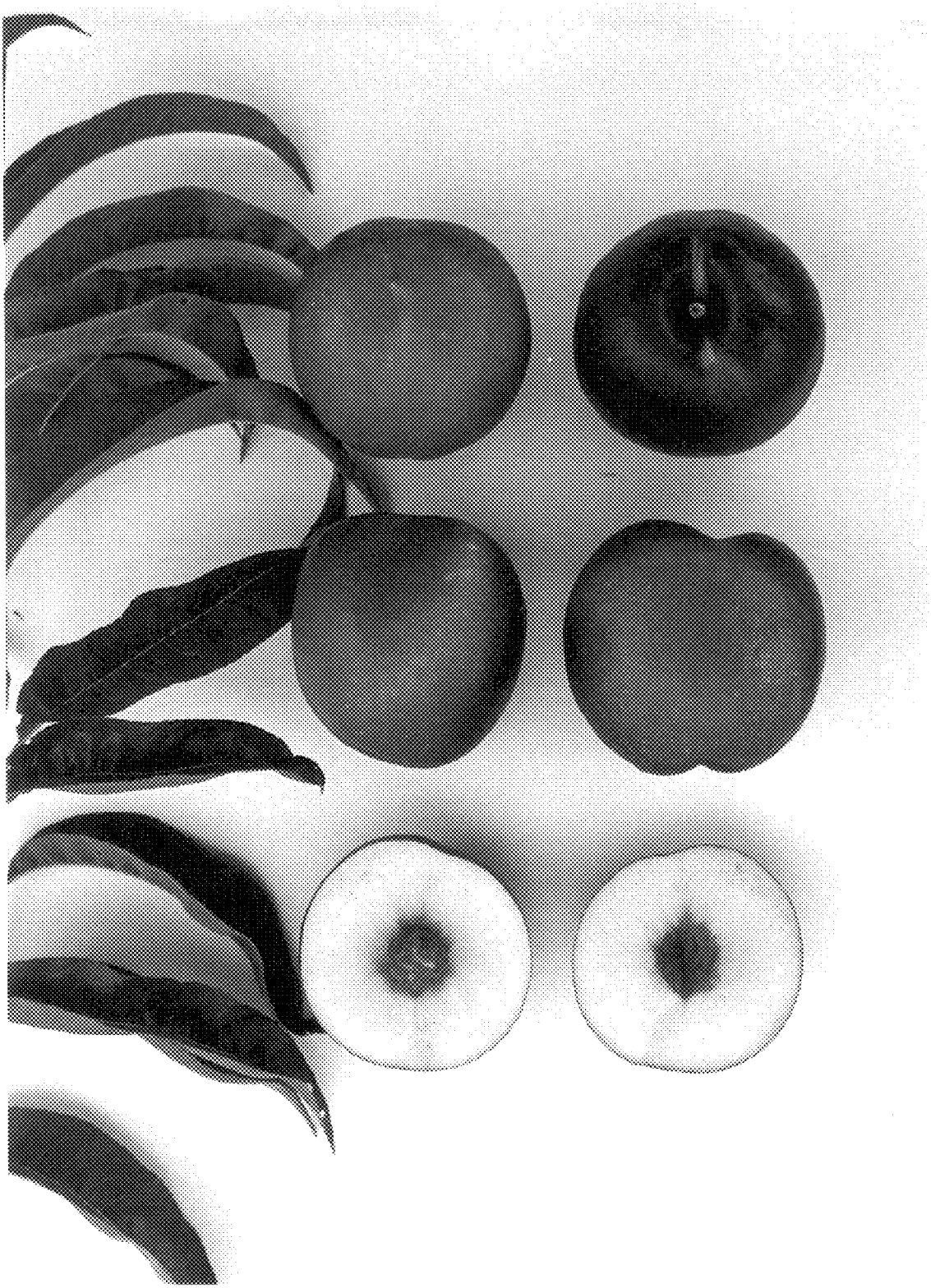

* * * * *